(12) United States Patent
Rajala et al.

(10) Patent No.: US 7,919,453 B2
(45) Date of Patent: *Apr. 5, 2011

(54) DOSAGE CAP ASSEMBLY FOR AN APPLICATOR

(75) Inventors: Gregory J. Rajala, Neenah, WI (US);
Daniel J. Heuer, Fremont, WI (US);
Steven C. Gehling, Oshkosh, WI (US);
Rebecca D. Hayes, Appleton, WI (US);
Elizabeth E. Bell, Appleton, WI (US);
Joyce A. Damico, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 513 days.

This patent is subject to a terminal disclaimer.

(21) Appl. No.: 11/090,560

(22) Filed: Mar. 25, 2005

(65) Prior Publication Data
US 2006/0213918 A1    Sep. 28, 2006

(51) Int. Cl.
*A01N 61/00* (2006.01)
*A61F 13/15* (2006.01)
*A61F 13/20* (2006.01)

(52) U.S. Cl. .................. 514/1; 604/385.17; 604/904

(58) Field of Classification Search .................. None
See application file for complete search history.

(56) References Cited

U.S. PATENT DOCUMENTS

| | | |
|---|---|---|
| 639,864 A | 12/1899 | Von Raitz |
| 706,778 A | 8/1902 | Pond |
| 749,220 A | 1/1904 | Pond |
| 812,768 A | 2/1906 | Pond |
| 812,769 A | 2/1906 | Pond |
| 812,770 A | 2/1906 | Pond |
| 1,234,383 A | 7/1917 | Pond |
| 1,395,295 A | 11/1921 | Pond |
| 1,538,678 A | 5/1925 | Blinn |
| 1,887,526 A | 11/1932 | Spielberg et al. |
| 2,473,368 A | 6/1949 | Flintermann |
| 2,696,456 A | 12/1954 | Hetterick |
| 2,739,593 A | 3/1956 | Mclaughlin |
| 2,854,978 A | 10/1958 | Millman et al. |
| 2,922,423 A | 1/1960 | Rickard et al. |
| 3,086,527 A | 4/1963 | Forrest |
| 3,415,249 A | 12/1968 | Sperti |
| 3,515,138 A | 6/1970 | Hochstrasser et al. |
| 3,521,637 A | 7/1970 | Waterbury |
| 3,760,808 A * | 9/1973 | Bleuer ................ 604/14 |
| 3,762,414 A | 10/1973 | Burnhill |
| 3,791,385 A | 2/1974 | Davis et al. |
| 3,796,219 A | 3/1974 | Hanke |
| 3,815,600 A | 6/1974 | Groves |
| 3,818,911 A | 6/1974 | Fournier |
| 3,830,237 A | 8/1974 | Bernardin et al. |
| 3,831,605 A | 8/1974 | Fournier |
| 3,884,233 A | 5/1975 | Summey |
| 3,885,564 A | 5/1975 | Groves |
| 3,902,493 A | 9/1975 | Baier et al. |
| 3,916,898 A | 11/1975 | Robinson |
| 3,918,452 A | 11/1975 | Cornfeld |
| 3,921,636 A | 11/1975 | Zaffaroni |
| 3,948,254 A | 4/1976 | Zaffaroni |
| 3,949,752 A | 4/1976 | Van Stee |
| 3,991,760 A | 11/1976 | Drobish et al. |
| 3,993,073 A | 11/1976 | Zaffaroni |
| 3,995,633 A | 12/1976 | Gougeon |
| 3,995,634 A | 12/1976 | Drobish |
| 3,995,636 A | 12/1976 | Murray et al. |
| 4,016,270 A | 4/1977 | Pharriss et al. |
| 4,077,407 A | 3/1978 | Theeuwes et al. |
| 4,077,408 A | 3/1978 | Murray et al. |
| 4,077,409 A | 3/1978 | Murray et al. |
| 4,159,719 A | 7/1979 | Haerr |
| 4,160,020 A | 7/1979 | Ayer et al. |
| 4,160,452 A | 7/1979 | Theeuwes |
| 4,186,742 A | 2/1980 | Donald |
| 4,237,888 A | 12/1980 | Roseman et al. |
| 4,260,570 A | 4/1981 | Ravel |
| 4,271,835 A | 6/1981 | Conn et al. |
| 4,286,596 A | 9/1981 | Rubinstein |
| 4,308,867 A | 1/1982 | Roseman et al. |
| 4,309,997 A | 1/1982 | Donald |

(Continued)

FOREIGN PATENT DOCUMENTS

DE        2 024 930        12/1971

(Continued)

OTHER PUBLICATIONS

Nagata, Shunji, "Capsule Technology," *Drug Delivery Technology*, vol. 2, No. 2, Mar./Apr. 2002, printed from Internet web page "www.drugdeliverytech.com," 8 pages.

(Continued)

*Primary Examiner* — Janet Epps-Smith
(74) *Attorney, Agent, or Firm* — Randall W. Fieldhack; Denise L. Stoker (57) ABSTRACT

A dosage cap assembly is provided for use with an applicator assembly, the dosage cap assembly including a tip including an outer surface, an attachment end, a second end, and an inner surface defining a tip cavity, wherein the attachment end of the tip includes an engagement mechanism. The dosage cap assembly also includes a cap having an inner surface defining a cap cavity, the inner surface generally conforming to the outer surface of the tip; and a dosage form disposed within the tip cavity.

8 Claims, 7 Drawing Sheets

U.S. PATENT DOCUMENTS

| | | | |
|---|---|---|---|
| 4,312,348 A | 1/1982 | Friese | |
| 4,317,447 A | 3/1982 | Williams | |
| 4,318,405 A | 3/1982 | Sneider | |
| 4,328,804 A | 5/1982 | Shimatani | |
| 4,340,055 A | 7/1982 | Sneider | |
| 4,341,211 A | 7/1982 | Kline | |
| 4,341,215 A | 7/1982 | Eldridge | |
| 4,373,631 A | 2/1983 | Friese et al. | |
| 4,383,993 A | 5/1983 | Hussain et al. | |
| 4,393,871 A | 7/1983 | Vorhauer et al. | |
| 4,402,695 A | 9/1983 | Wong | |
| 4,405,323 A | 9/1983 | Auerbach | |
| 4,421,504 A | 12/1983 | Kline | |
| 4,439,194 A | 3/1984 | Harwood et al. | |
| 4,483,846 A | 11/1984 | Koide et al. | |
| 4,551,148 A | 11/1985 | Riley, Jr. et al. | |
| 4,553,965 A | 11/1985 | Conn et al. | |
| 4,560,549 A | 12/1985 | Ritchey | |
| 4,582,717 A | 4/1986 | Von Bittera et al. | |
| 4,601,714 A | 7/1986 | Burnhill | |
| 4,610,659 A * | 9/1986 | Friese | 604/11 |
| 4,649,075 A | 3/1987 | Jost | |
| 4,690,671 A | 9/1987 | Coleman et al. | |
| 4,693,705 A | 9/1987 | Gero | |
| 4,795,422 A | 1/1989 | Conner et al. | |
| 4,871,542 A | 10/1989 | Vilhardt | |
| 4,922,928 A | 5/1990 | Burnhill | |
| 4,923,440 A | 5/1990 | Genaro | |
| 4,979,947 A | 12/1990 | Berman | |
| 4,983,393 A | 1/1991 | Cohen et al. | |
| 5,002,540 A | 3/1991 | Brodman et al. | |
| 5,041,080 A | 8/1991 | Shimatani et al. | |
| 5,069,906 A | 12/1991 | Cohen et al. | |
| 5,070,889 A | 12/1991 | Leveen et al. | |
| 5,084,277 A | 1/1992 | Greco et al. | |
| 5,116,619 A | 5/1992 | Greco et al. | |
| 5,201,326 A | 4/1993 | Kubicki et al. | |
| 5,213,566 A | 5/1993 | Weissenburger | |
| 5,273,521 A | 12/1993 | Peiler et al. | |
| 5,295,984 A | 3/1994 | Contente et al. | |
| 5,299,581 A | 4/1994 | Donnell et al. | |
| 5,330,427 A | 7/1994 | Weissenburger | |
| 5,330,761 A | 7/1994 | Baichwal | |
| 5,362,498 A | 11/1994 | Aiache | |
| 5,383,891 A | 1/1995 | Walker | |
| 5,393,528 A | 2/1995 | Staab | |
| 5,417,224 A | 5/1995 | Petrus et al. | |
| 5,466,463 A | 11/1995 | Ford | |
| 5,527,534 A | 6/1996 | Myhling | |
| 5,529,782 A | 6/1996 | Staab | |
| 5,542,914 A | 8/1996 | Van Iten | |
| 5,612,051 A | 3/1997 | Yue | |
| 5,646,206 A | 7/1997 | Coffin et al. | |
| 5,676,647 A * | 10/1997 | Cimber | 604/11 |
| 5,683,358 A | 11/1997 | Nielsen et al. | |
| 5,769,813 A | 6/1998 | Peiler et al. | |
| 5,788,980 A | 8/1998 | Nabahi | |
| 5,840,055 A | 11/1998 | Sgro | |
| 5,912,006 A | 6/1999 | Bockow et al. | |
| 5,958,461 A | 9/1999 | Larsen | |
| 5,988,386 A * | 11/1999 | Morrow | 206/581 |
| 5,993,856 A | 11/1999 | Ragavan et al. | |
| 6,036,666 A | 3/2000 | Peiler et al. | |
| 6,039,968 A | 3/2000 | Nabahi | |
| 6,086,909 A | 7/2000 | Harrison et al. | |
| 6,096,332 A | 8/2000 | Yang | |
| 6,103,256 A | 8/2000 | Nabahi | |
| 6,126,959 A | 10/2000 | Levine et al. | |
| 6,197,327 B1 | 3/2001 | Harrison et al. | |
| 6,200,288 B1 | 3/2001 | Heaton et al. | |
| 6,203,514 B1 | 3/2001 | Clifford | |
| 6,264,638 B1 | 7/2001 | Contente | |
| 6,264,972 B1 | 7/2001 | Drury | |
| 6,316,019 B1 | 11/2001 | Yang | |
| 6,328,991 B1 | 12/2001 | Myhling | |
| 6,416,778 B1 | 7/2002 | Ragavan et al. | |
| 6,416,779 B1 | 7/2002 | D'Augustine et al. | |
| 6,524,269 B2 | 2/2003 | Mcnamara | |
| 6,526,980 B1 | 3/2003 | Tracy et al. | |
| 6,558,362 B1 | 5/2003 | Chaffringeon | |
| 6,582,389 B2 | 6/2003 | Buzot | |
| 6,592,540 B2 | 7/2003 | Decarlo | |
| 6,958,057 B2 * | 10/2005 | Berg et al. | 604/385.17 |
| 7,708,726 B2 * | 5/2010 | Hayes et al. | 604/385.17 |
| 2002/0161088 A1 | 10/2002 | Kochvar et al. | |
| 2002/0193726 A1 | 12/2002 | Cimber | |
| 2003/0028177 A1 | 2/2003 | Berg et al. | |
| 2003/0045829 A1 * | 3/2003 | Gehling et al. | 604/11 |
| 2003/0139709 A1 * | 7/2003 | Gehling | 604/365 |
| 2003/0144639 A1 | 7/2003 | Gehling | |
| 2004/0043061 A1 | 3/2004 | Leon et al. | |
| 2004/0224008 A1 | 11/2004 | Zhang | |
| 2006/0213919 A1 | 9/2006 | Heuer et al. | |
| 2006/0216334 A1 | 9/2006 | Gehling et al. | |
| 2006/0217652 A1 | 9/2006 | Heuer et al. | |

FOREIGN PATENT DOCUMENTS

| | | |
|---|---|---|
| DE | 2 309 575 A | 9/1974 |
| DE | 3 248 152 A1 | 6/1984 |
| EP | 0 110 793 B1 | 3/1987 |
| EP | 0 747 045 A2 | 12/1996 |
| EP | 0 962 201 A1 | 12/1999 |
| GB | 2 277 447 A | 11/1994 |
| JP | 02-212431 A | 8/1990 |
| JP | 07-000450 A | 1/1995 |
| WO | WO 79/00014 A1 | 1/1979 |
| WO | WO 82/02489 A1 | 8/1982 |
| WO | WO 82/04185 A1 | 12/1982 |
| WO | WO 87/02576 A1 | 5/1987 |
| WO | WO 94/08536 A1 | 4/1994 |
| WO | WO 97/19680 A1 | 6/1997 |
| WO | WO 97/45066 A1 | 12/1997 |
| WO | WO 99/47121 A1 | 9/1999 |
| WO | WO 99/48453 A1 | 9/1999 |
| WO | WO 00/66213 A1 | 11/2000 |
| WO | WO 01/13836 A1 | 3/2001 |
| WO | WO 01/80937 A1 | 11/2001 |
| WO | WO 02/03896 A1 | 1/2002 |
| WO | WO 02/09631 A1 | 2/2002 |
| WO | WO 02/051718 A1 | 7/2002 |
| WO | WO 03/007862 A2 | 1/2003 |
| WO | WO 03/020240 A2 | 3/2003 |
| WO | WO 03/037381 A1 | 5/2003 |
| WO | WO 03/059318 A2 | 7/2003 |
| WO | WO 2006/104631 A1 | 10/2006 |

OTHER PUBLICATIONS

Patent Abstracts of Australia AU-A-32971/95: Description of Trevor William Lucas, "Herbal Tampon."

Derwent World Patent Database abstract of ZA 87/9748 A: Description of D. Eyal, "Tampon."

* cited by examiner

DOSAGE CAP ASSEMBLY FOR AN APPLICATOR

BACKGROUND

This invention pertains to a dosage cap assembly for an applicator used for the application of various therapeutic treatments or other non-medicinal preparations into the vaginal or other cavity and methods to provide such assemblies.

Many disease states and physiological conditions may occur in a woman, including symptoms associated with premenstrual syndrome, menstruation, and menopause. These symptoms may include dysmenorrhea (menstrual cramping), irritability, water retention, moodiness, depression, anxiety, skin changes, headaches, breast tenderness, tension, weight gain, cravings, fatigue, hot flashes, itching, and other associated sensory maladies.

Many of these symptoms are due to changes in hormonal levels throughout the menstrual cycle. One example that affects a large number of post-pubescent women is dysmenorrhea, which is the occurrence of painful uterine cramps during menstruation. Menstrual cramping is associated with increased levels of prostaglandin F2α, prostaglandin E2, and, in some cases, leukotrienes in the endometrium and menstrual fluid. These eicosinoids lead to restricted blood flow to the uterus and increased uterine contractions, causing pain.

Various analgesics may be effective in limiting the pain from dysmenorrhea; however some orally-delivered analgesics can cause nausea and vomiting or other untoward side effect therefore alternative routes of analgesic delivery are of interest.

Attempts have been made to deliver analgesics in the vicinity of the cervix and the vaginal mucosa using various vaginally-inserted devices and methods. Because many of these symptoms typically occur in conjunction with menstruation, some have tried to combine an analgesic with a tampon by coating the tampon, dipping the tampon, or by combining the analgesic with the tampon materials.

For example, in a method of preparation of such a product appropriate for a laboratory setting, a formulation of a fatty compound excipient and an analgesic are heated to a liquid state. Constant mixing of the heated formulation is required to produce a homogeneous formulation. The formulation is then poured onto the tip of a tampon held in a form to contain the liquid. As the formulation cools, the ingredients solidify into a solid waxy substance that has adhered to the absorbent material of the tampon and is thereby securely fastened to the tip of the tampon.

SUMMARY OF THE INVENTION

Several problems are inherent in a process that attempts to introduce a formulation including a therapeutic agent into or onto a tampon by coating, dipping, solidifying, or the like. Processes such as these may work in a laboratory setting but may not be feasible within an automated tampon manufacturing process. Because of dosing requirements, the formulation including a therapeutic agent must be maintained in a solution that is both homogeneous and of the proper purity to ensure consistent concentration of the therapeutic agent. These requirements are difficult to accomplish during production operation of an automated tampon manufacturing process, and are significantly more difficult to maintain when the automated tampon manufacturing process stops. In addition, different styles and sizes of tampons may have different densities and will absorb an applied liquid formulation including a therapeutic agent differently, resulting in variability in the abilities of the tampons to release the therapeutic agent across such different tampons.

Specifically, the need to provide constant agitation or mixing of the formulation including a therapeutic agent poses challenges as to how to keep a therapeutic agent homogeneously suspended in a solution when the automated tampon manufacturing process stops. The use of inline mixers and recirculation of the heated liquid formulation during machine stops may provide a method to keep the formulation moving and mixed. However, because a machine could be stopped for several hours, the stability of some formulation mixtures may be compromised by long durations at elevated temperatures, or by mechanical shear forces due to the continuous pumping of the recirculating liquid.

In addition, environmental conditions, especially during shipping and/or storage, may cause some formulations including a therapeutic agent to melt and absorb into the tampon and/or onto the packaging material prior to use, thus making the therapeutic agent less available for use.

The advantages of using a pre-manufactured dosage cap assembly over an in-line process where the medicated ingredients are applied to the tampon coincident with the tampon manufacturing process are numerous. The dosage form would be desirably produced at a pharmaceutical manufacturer whose manufacturing facility meets current regulatory and quality requirements for drugs and/or devices as appropriate. This could ensure that a therapeutic agent with the correct dose and purity is homogeneously dispersed within the dosage form. The use of a dosage cap simplifies the modifications to an existing tampon manufacturing process. The use of a dosage cap allows multiple types of therapeutic agents to be applied to the tampon. The chemical and physical stabilities of the dosage form are not compromised by the assembly process of applying the dosage form onto the tampon assembly. Further, the dosage form is kept separate from the tampon throughout the transportation and storage cycle until it is ready to use and thus does not allow any of the therapeutic agent to be potentially absorbed into the tampon. The dosage form manufacturing process is less dependent on the physical characteristics of the absorbent structure of the tampon because the dosage form is not required to bond with the tampon.

The present invention relates to a therapeutic agent delivery system that may be integral with or associated with a feminine care product. The therapeutic agent delivery system including the therapeutic agent and excipients may be any therapeutic agent that will be absorbed into the body through the vaginal or other epithelium, or deposited topically on the vaginal or other epithelium, for the purposes of treating a physiological disease, state, or condition.

The present invention solves these problems by coupling a dosage cap assembly to a tampon assembly to form a medicated tampon assembly. The dosage form is solid or semi-solid at room temperature and is sufficiently stable that it may be manufactured separately in a controlled facility, whereby the dosage including a therapeutic agent is easily controlled through controls on homogeneity, concentration, and purity.

More specifically, the present invention provides a dosage cap assembly for use with an applicator assembly. The dosage cap assembly includes a tip including an outer surface, an attachment end, a tip second end, and an inner surface defining a tip cavity, wherein the attachment end of the tip includes an engagement mechanism, and a dosage form disposed within the tip cavity. The assembly also includes a cap having an inner surface defining a cap cavity, the inner surface generally conforming to the outer surface of the tip. The assembly may also include a barrier seal.

In another aspect, the present invention provides a delivery device including an applicator having a first member with a receiving end and an insertion end and an inner tube slidably received in the receiving end; a dosage cap assembly including a tip; and an engagement mechanism having a first portion and a second portion, wherein one of the tip and the insertion end includes the first portion of the engagement mechanism, and the other of the tip and the insertion end includes the second portion of the engagement mechanism.

In another aspect, the present invention provides a kit for treating a physiological condition, the kit including a tampon assembly; and a dosage cap assembly, wherein the dosage cap assembly includes a tip, the tip including an outer surface and an inner surface, the inner surface defining a tip cavity, wherein the tip includes an engagement mechanism; a cap having an inner surface defining a cap cavity, wherein the tip is disposed within the cap cavity; a dosage form disposed within the tip cavity; and a barrier seal affixed to the cap.

In another aspect, the present invention relates to a method for producing a delivery device, the method including producing a dosage cap assembly, wherein the dosage cap assembly includes a tip, the tip including an outer surface and an inner surface, the inner surface defining a tip cavity, wherein the tip includes an engagement mechanism; a cap having an inner surface defining a cap cavity, wherein the tip is disposed within the cap cavity; a dosage form disposed within the tip cavity; and a barrier seal affixed to the cap. The method also includes sealing the dosage cap assembly and packaging the dosage cap assembly.

In another aspect, the present invention relates to a method for providing a delivery device, the method including providing a sealed dosage cap assembly to a consumer, wherein the dosage cap assembly includes a tip, the tip having an outer surface and an inner surface, the inner surface defining a tip cavity, wherein the tip includes an engagement mechanism; a cap having an inner surface defining a cap, wherein the tip is disposed within the cap cavity; a dosage form disposed within the cavity; and a barrier seal affixed to the cap. The method also includes instructing the consumer to combine the dosage cap assembly with a tampon assembly.

Other objects and advantages of the present invention will become more apparent to those skilled in the art in view of the following description and the accompanying drawings.

DETAILED DESCRIPTION OF THE PREFERRED EMBODIMENTS

The invention as described herein will be described for exemplary purposes using a tampon as an example of a feminine care product. The invention, however, applies equally to other forms of products, including tampons and vaginally-inserted devices, and should not be limited to the example described herein. In addition, although the example described includes a tampon with absorbent material, a product without absorbent material, such as a tampon applicator or other similar applicator, is also contemplated within the invention. Also contemplated is the use of the invention described herein in conjunction with non-catamenial feminine products such as incontinence products, including female incontinence inserts.

The term "surface" and its plural generally refer herein to the outer or the topmost boundary of an object.

The term "dosage form" is used herein as a generic term for a unit form of a formulation that includes a therapeutic agent. The dosage form includes a discrete and consistent quantity of the therapeutic agent to allow for consistent dosing of one receiving the dosage form. The dosage form may be a suppository, a capsule, a tablet, a gel, or any other suitable form. The dosage form may also be spherical, ovoid, domal, generally flat, or any other suitable shape dictated by the needs of the application of the dosage form. The dosage form may have convex, concave, planar, arcuate, or any other suitable surfaces as dictated by the needs of the application of the dosage form.

Figure 1:
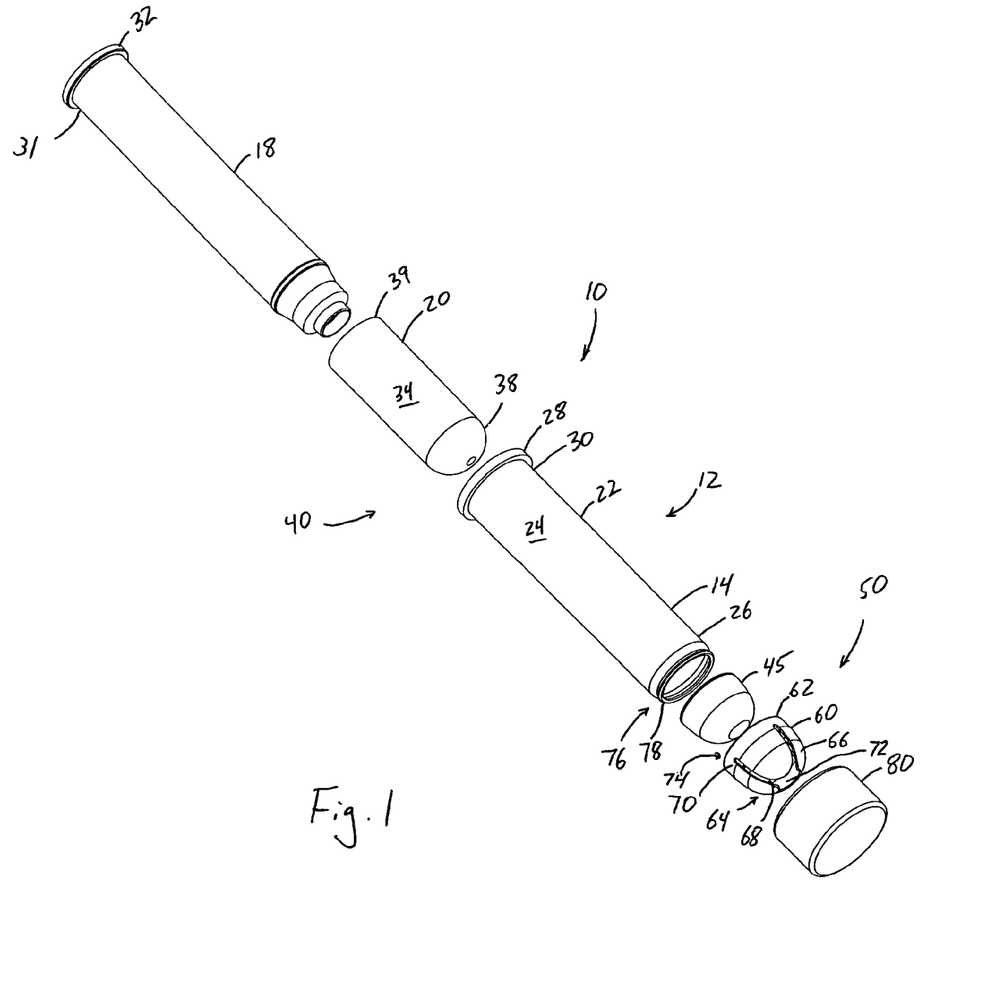
FIG. 1 is an exploded perspective view of a medicated tampon assembly including a medicated tampon of the present invention.

FIG. 1 illustrates a delivery device in the form of a medicated tampon assembly 10 that includes a tampon assembly 40 and a dosage cap assembly 50. The tampon assembly 40 includes a tampon applicator 12 and a catamenial tampon 20. The tampon applicator 12 includes a first member or outer tube 14 and a second member or inner tube 18, where the tampon applicator 12 is designed to house the tampon 20 and provide a comfortable means of inserting the tampon 20 into a woman's vagina. The medicated tampon assembly 10 also includes a dosage cap assembly 50 designed to couple to the first member 14, as is described in more detail below. In another aspect of the present invention, the tampon assembly 40 or the tampon applicator 12 may be referred to simply as an applicator, particularly if the tampon assembly 40 does not include a tampon 20, or if the tampon applicator 12 is not associated with a tampon 20.

The tampon applicator 12 includes a first member 14 and a second member 18. The first member 14 may be in the form of a spirally wound, convolutely wound or longitudinally seamed hollow tube which is formed from paper, paperboard, cardboard, plastic, other suitable material, or a combination of such materials. Any plastic in the first member 14 is preferably polyethylene, but may be polypropylene or other suitable plastic. The first member 14, also commonly referred to as an outer tube, may be of any suitable dimensions necessary to house a particular size of tampon 20. The first member 14 has a wall 22 with an outside or exterior surface 24.

The first member 14 is sized and configured to house the tampon 20, and should have a substantially smooth exterior surface 24 which will facilitate insertion of the first member 14 into a woman's vagina. When the exterior surface 24 is smooth and/or slippery, the first member 14 will easily slide into a woman's vagina without subjecting the internal tissues of the vagina to abrasion. The first member 14 may be coated to give it a high slip characteristic. Wax, polyethylene, a combination of wax and polyethylene, cellophane and clay are representative coatings that may be applied to the first member 14 to facilitate comfortable insertion. The first member 14 itself may be formulated to give it a high slip characteristic, including the addition of additives to the resin from which the first member is made, or by an alteration in physical structure of the exterior surface 24, such as adding pebbling or other bumps, to decrease the amount of surface area in contact with the vaginal or other epithelium.

Referring to FIG. 1, an insertion end 26 is shown having an opening of a diameter approximately equal to the diameter of the first member 14, but the diameter of the opening at the insertion end may be larger or smaller than the diameter of the first member 14. The insertion end 26 has part of an engagement mechanism 76 (described in more detail below) to facilitate attachment of the dosage cap assembly 50 to the first member 14.

As stated above, the medicated tampon assembly 10 includes a second member 18, also commonly referred to as an inner tube. The second member 18, like the first member 14, may be a spirally wound, a convolutely wound or a longitudinally seamed hollow tube constructed from paper, paperboard, cardboard, plastic, other suitable material, or a combination thereof. The second member 18 may be constructed of the same material as the first member 14 or it may be made out of a different material. The second member 18 may also be a solid stick or use some other unique shape. It is also possible to form a finger flange 32 on the free end 31 of the second member 18 to provide an enlarged surface onto which the user's forefinger may rest. The finger flange 32 thereby functions as a seat for the forefinger and facilitates movement of the second member 18 into the first member 14. The first member 14 may have a fingergrip ring 28 located proximate the receiving end 30. The fingergrip ring 28 provides an enlarged surface onto which one or more fingers of the user may rest. In use, the user may position one or more fingers on the fingergrip ring 28 and one or more fingers on the finger flange 32. The user then holds the fingergrip ring 28 and pushes the finger flange 32 to move the second member 18 toward and into the first member 14.

A tampon 20 is an absorbent member primarily designed to be worn by a woman during her menstrual period to absorb menses and other body fluids. The tampon 20 includes a tampon body 34 and a withdrawal string (not shown). The tampon body 34 is normally compressed into the form of a cylinder and may have a blunt, rounded or shaped forward end. The tampon body 34 has a forward or distal end 38 that is closer to the cervix when the tampon 20 is in use. The tampon body 34 also has a proximal end 39 that is closer to the vaginal opening when the tampon 20 is in use. The tampon 20 commonly has a withdrawal string fastened to the tampon body 34 and extending from the proximal end 39. The withdrawal string serves as a means for withdrawing the tampon 20 from the woman's vagina. Catamenial tampons suitable for use in the present invention include any absorbent material as is known in the art. The distal end 38 of the tampon body 34 or the tampon body 34 itself may be formed into specific shapes such as various cup shapes to enhance the therapeutic agent contact area with the cervix, anterior fornix, posterior fornix, lateral fornices, vaginal epithelium areas, or conformance to other anatomical areas within the vaginal or other cavity.

In another aspect of the present invention (not shown), the tampon applicator 12 may be produced without a tampon 20. Such a configuration is similar to that described above. In such case the tampon applicator assembly 10 is herein referred to as an applicator assembly.

Figure 2:
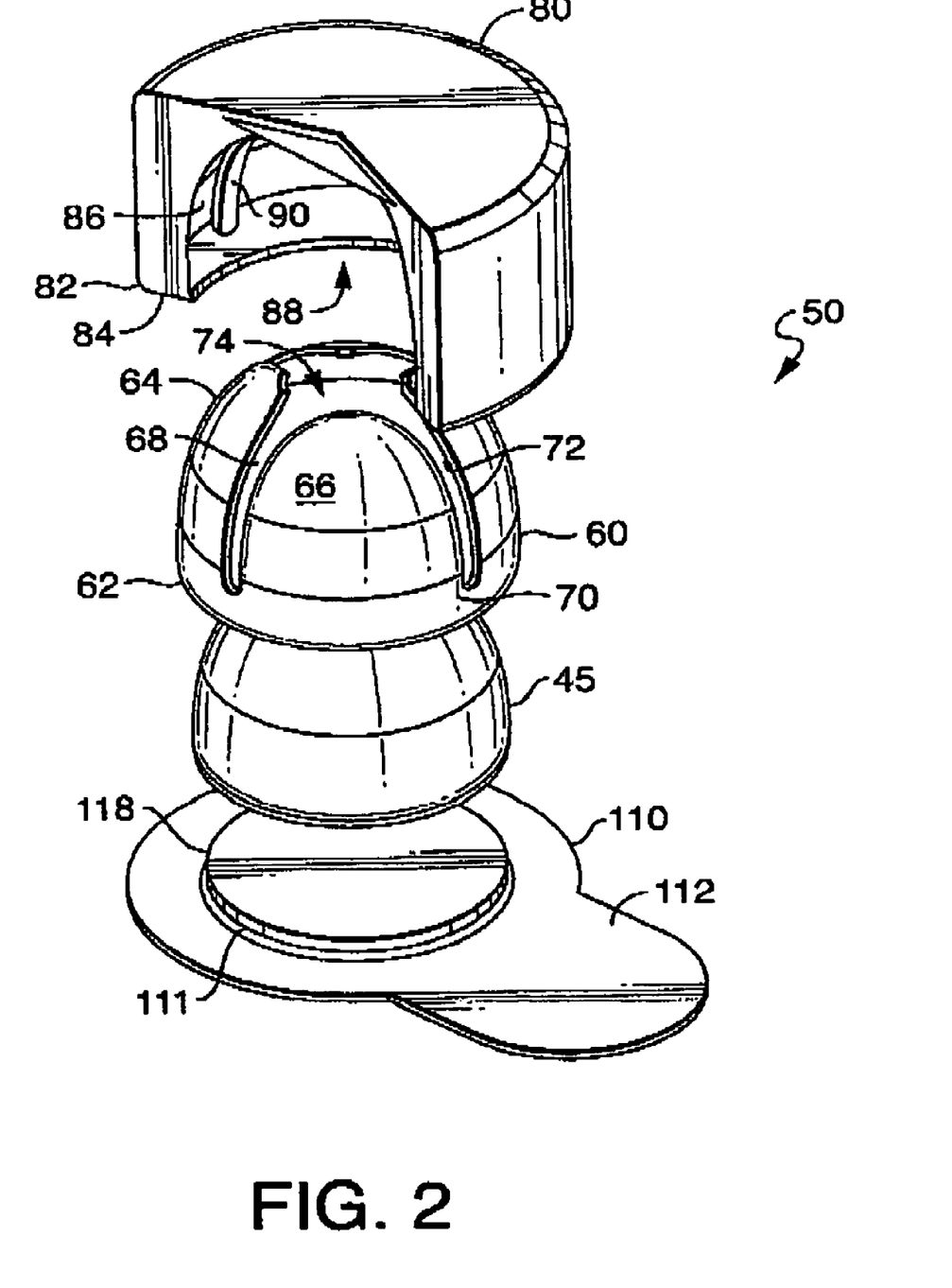
FIG. 2 is an exploded partially cutaway perspective view of a dosage cap assembly with a barrier seal to be used in conjunction with the medicated tampon assembly of FIG. 1.

A medicated tampon assembly 10 includes the tampon 20 and a therapeutic agent included in a dosage form 45, which is typically located within a dosage cap assembly 50. The dosage cap assembly 50 includes a tip 60, a cap 80 enclosing the tip 60, and a dosage form 45 positioned within the tip 60. As shown in FIG. 2, a barrier seal 110 may also be employed to seal the dosage form 45 within the tip 60, or the dosage form 45 and the tip 60 within the cap 80.

Figure 3:
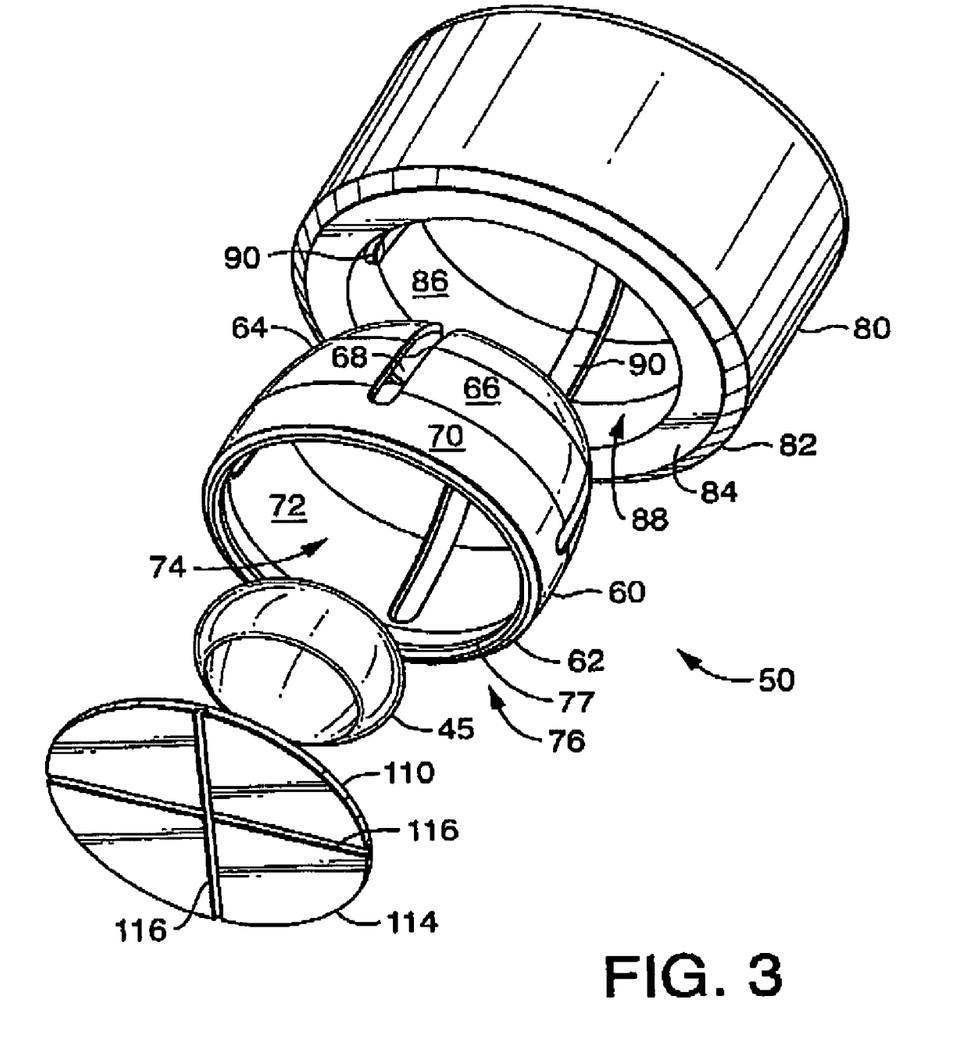
FIG. 3 is an exploded perspective view of a dosage cap assembly with a frangible barrier to be used in conjunction with the medicated tampon assembly of FIG. 1.
Figure 7:
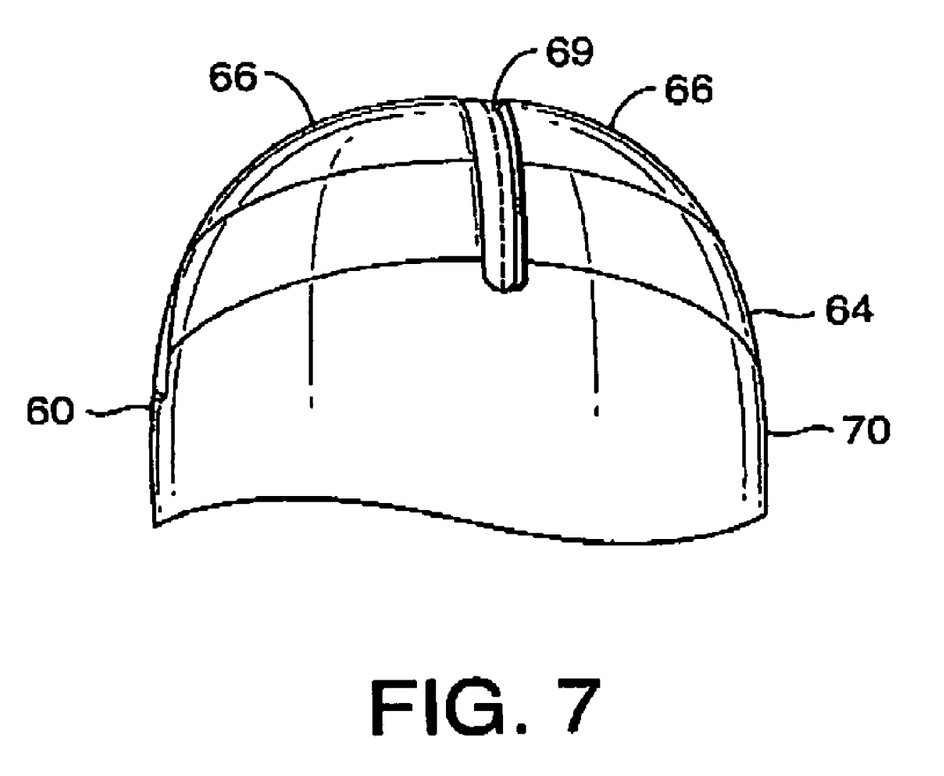
FIG. 7 is a partial perspective view of another aspect of a tip for use with the medicated tampon assembly of FIG. 1.

Referring to FIGS. 2 and 3, the dosage cap assembly 50 includes a tip 60 with an attachment end 62 and a tip second end 64. The tip 60 may include a plurality of pleats or petals 66 at the tip second end 64 that may radially open such that the tip 60 has a diameter approximately equal to or greater than the diameter of the first member 14. The petals 66 may be either even or odd in number and may be equally spaced apart or non-uniformly arranged. Between any two petals 66 is a gap 68 that provides additional flexibility to the petals 66. As shown in FIG. 7, and in another aspect of the present invention, the gaps 68 may be filled by a frangible portion 69 such that the tip second end 64 is closed by petals 66 and frangible portions 69 until force applied by the dosage form 45, the tampon 20, or the second member 18 causes the frangible portions 69 to break, allowing the petals 66 to open.

The tip 60 also includes a tip outer surface 70 and a tip inner surface 72, where the tip inner surface 72 defines and at least partially encloses a tip cavity 74. The tip 60 is preferably manufactured from material similar to that of the first member 14, but any suitable material that will not adversely interact with the dosage form 45 may be used.

The attachment end 62 of the tip 60 includes an engagement mechanism 76 (shown in FIGS. 1, 3, 5, and 6) that allows the tip 60 to be attached to the first member 14 with minimal force. The attachment provided by the engagement mechanism 76 is preferably one-way or permanent for the improved structural integrity of the tip 60 with the first member 14 in use. In most types of engagement mechanisms suitably applied in such an application, the engagement mechanism 76 typically includes a first portion 77 and a second portion 78, where the first portion 77 engages with the second portion 78 to complete the engagement mechanism 76. The first portion 77 is positioned on one of the tip 60 or the first member 14, and the second member 78 is positioned on the other of the tip 60 or the first member 14.

Figure 5:
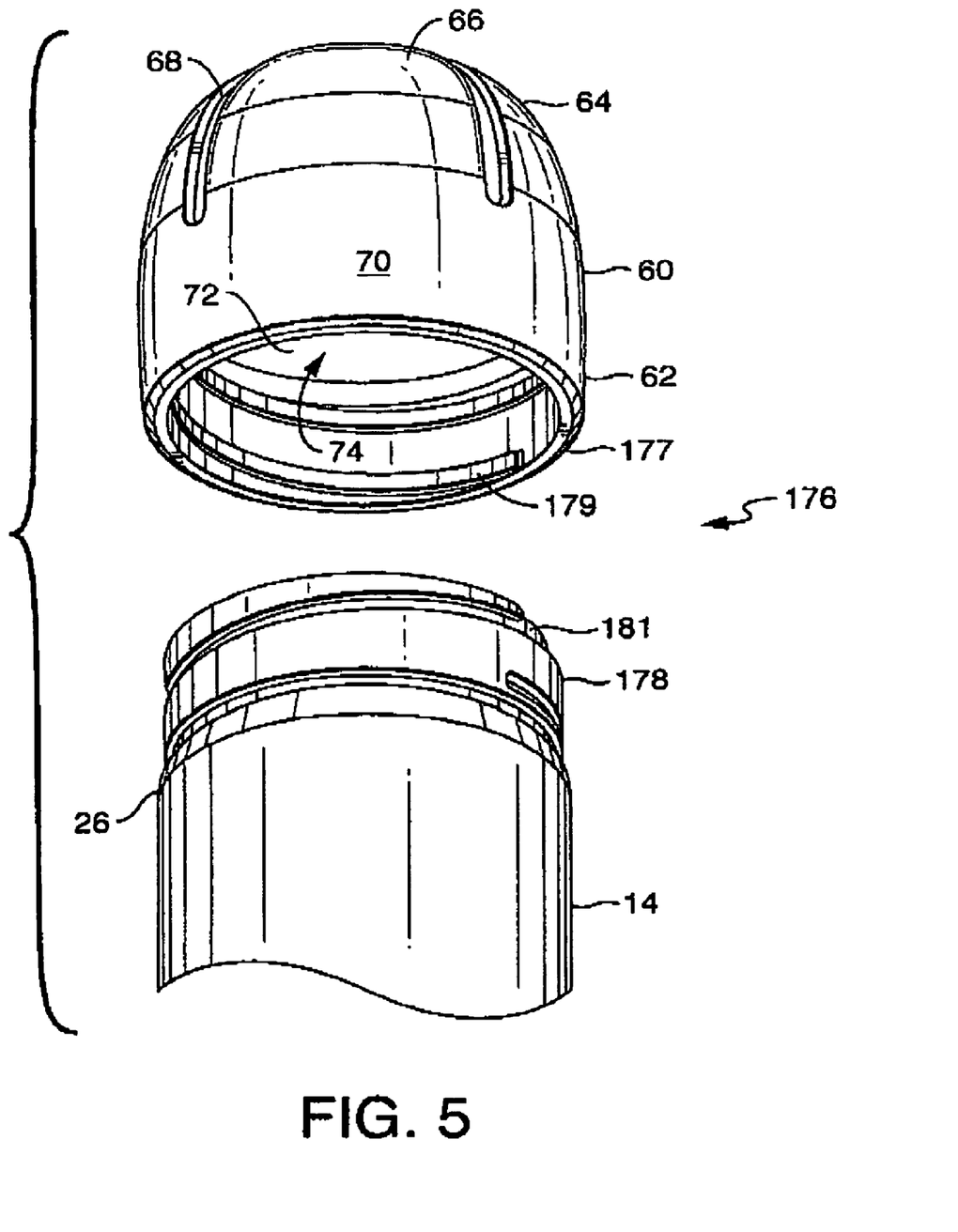
FIG. 5 is a partial perspective view of an engagement mechanism for the medicated tampon assembly of FIG. 1.

In an example of a screw-type engagement mechanism 176 illustrated in FIG. 5, the tip 60 includes a first portion 177 including helically-positioned projections 179, and the first member 14 includes a second portion 178 including helically-positioned projection-receiving spaces 181. The tip 60 is moved toward and twisted onto the first member 14 such that the helically-positioned projections 179 engage or interlock with the projection-receiving spaces 181. In another aspect of this example (not shown), the first portion 177 including helically-positioned projections 179 is positioned on the first member 14, and the second portion 178 including helically-positioned projection-receiving spaces 181 is positioned on the tip 60.

Figure 6:
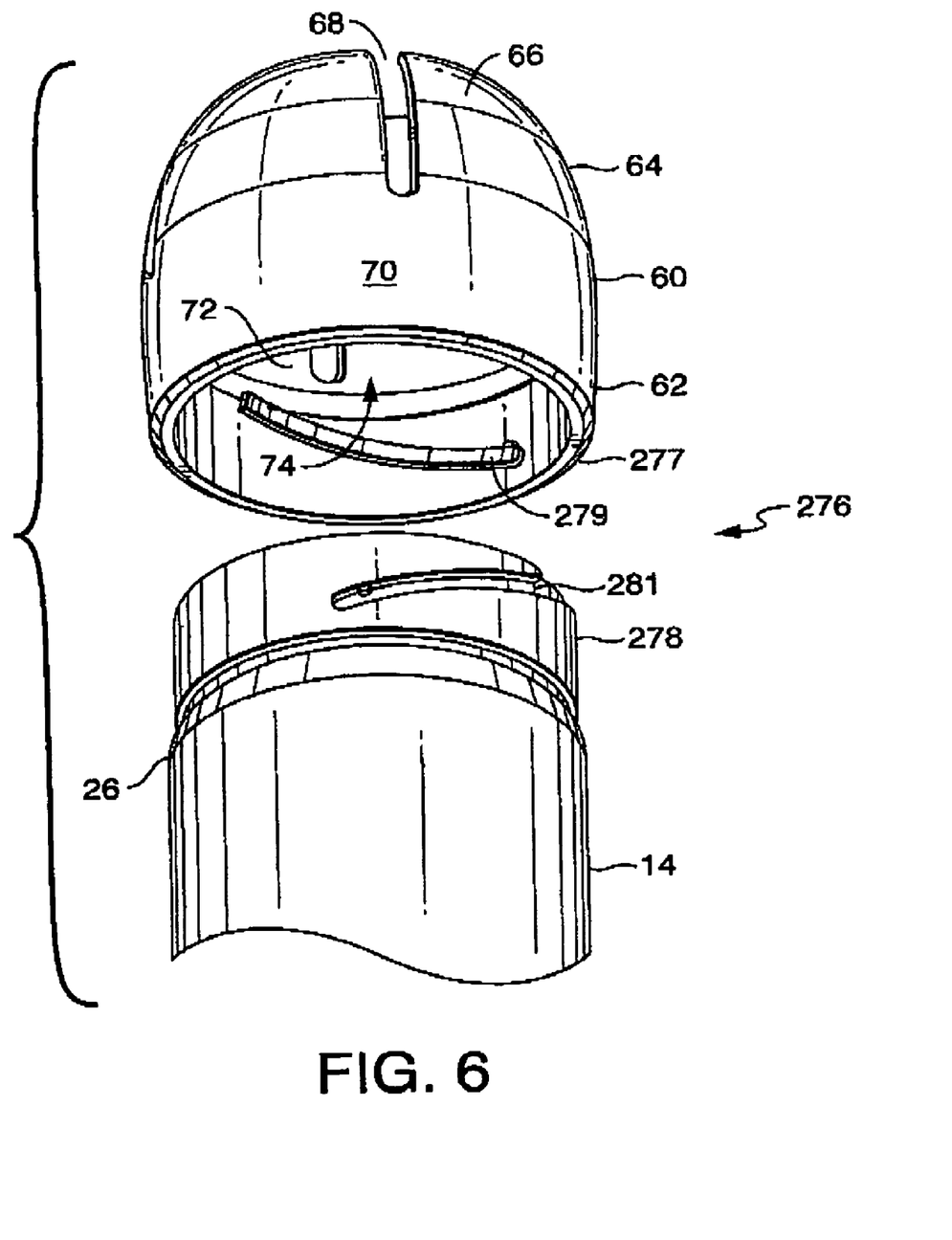
FIG. 6 is a partial perspective view of another aspect of an engagement mechanism for the medicated tampon assembly of FIG. 1.

In an example of a quarter-turn-type engagement mechanism 276 illustrated in FIG. 6, the tip 60 includes a first portion 277 including a helically-positioned projection 279, and the first member 14 includes a second portion 278 including a helically-positioned projection-receiving space 281. The tip 60 is moved toward and twisted onto the first member 14 such that the helically-positioned projection 279 engages or interlocks with the projection-receiving space 281. In another aspect of this example (not shown), the first portion 277 including a helically-positioned projection 279 is positioned on the first member 14, and the second portion 278 including a helically-positioned projection-receiving space 281 is positioned on the tip 60.

The engagement mechanism 76 between the tip 60 and the first member 14 are shown in FIGS. 1 and 3 as having a snap-on engagement profile. Such a profile is convenient to manufacture, may be assembled with minimal force, and creates the one-way attachment preferred for the structural integrity of this product. The engagement mechanism 76 may be any other suitable mechanism, including, but not limited, to a snap ring, conventional screw threads, quarter-turn threads, a mechanical latch, and an escapement-type mechanism.

Referring to FIGS. 2 and 3, the dosage cap assembly 50 may also include a cap 80 provided to enclose and protect the tip 60. The cap 80 is shown as being generally cylindrical, but the shape is not essential to the invention described herein and any suitable shape may be used. In alternate aspects, the cap 80 may be generally triangular or square or have a flattened side to inhibit the medicated tampon assembly 10 from rolling on a hard surface such as a countertop. The cap 80 includes an open end 82, an open end surface 84, and a cap inner surface 86 that defines and at least partially encloses a cap cavity 88. The cap cavity 88 projects inwardly from the open end 82. The cap 80 may be manufactured from polyethylene, rubber, or other similar materials that will not adversely interact with the dosage form.

The cap 80 may also include rib-like projections 90 projecting inwardly from the cap inner surface 86. The projections 90 are of such a shape and size to align with and generally fill the gaps 68 in the tip 60. Sealing the gaps enhances the ability to place the dosage form 45 into the tip 60 of the dosage cap assembly 50, and provides containment and protection of the dosage form 45. The projections 90 thereby provide at least a partial seal of the tip second end 64. The projections 90 may also serve to assist in holding the tip 64 in place within the cap cavity 88. The cap cavity 88 is sized and shaped such that the tip 60 fits entirely within the cap cavity 88, preferably with cap inner surface 86 reflecting the shape of the outer surface 70 of the tip 60 such that the outer surface 70 of the tip 60 maintains general contact with the cap inner surface 86. Unlike the tip 60, the cap 80 is removable and is necessarily removed prior to use of the medicated tampon assembly 10 by a consumer.

The dosage cap assembly 50 includes a dosage form 45 disposed therein. The dosage form 45 is disposed within the tip cavity 74 and may be shaped to generally conform to the inner surface 72 of the tip 60. In other aspects of the present invention, any other suitable shape may be used. The dosage form 45 may be formed directly within the tip cavity 74 by depositing a formulation including a therapeutic agent directly into the tip cavity 74. Alternatively, the dosage form 45 may also be pre-manufactured in the same or separate facility and then placed within the tip cavity 74 during manufacture of the dosage cap assembly 50. Further detail concerning the manufacture of dosage forms 45 is disclosed in co-pending U.S. patent application Ser. No. 10/335,816 filed on Dec. 31, 2002 and titled "Medicated Tampon".

In one aspect of the present invention, the dosage form 45 may be produced in any suitable form including, but not limited to, tablets, capsules, suppositories, gels, disks, lozenges, films, coatings, and other forms. In an alternate aspect of the present invention, the dosage form 45 may be produced in encapsulated form.

In another aspect of the present invention, the tablet, suppository, or capsule may be designed to melt at approximately body temperature, or to dissolve or otherwise disperse in the presence of a sufficient aqueous or other liquid trigger, or appropriate chemistry, such as a suitable pH.

In an additional aspect of the present invention, the dosage form 45 may be formed in any shape to promote contact with anatomical structures such as the vaginal epithelium, the anterior fornix, the posterior fornix, lateral fornices, the cervix, or other structures.

The dosage form 45 may include any therapeutic agent, along with any excipients, compounds, or other ingredients that are desirable to introduce into the vaginal or other cavity to promote the functionality of that therapeutic agent. The excipients may assist the release of the therapeutic agent, or assist in the absorbency of the therapeutic agent into the vaginal or other epithelium. The use of excipients to facilitate the formulation, delivery, stability, and aesthetic properties of a therapeutic agent delivery system is well known to those familiar with the art. Examples of ingredients that may accompany the therapeutic agent in the dosage form 45 include excipients, biologically-compatible adhesives, surfactants, and penetration enhancers. An example of a suitable excipient is SUPPOCIRE suppository base, available from Gattefossé Corp. SUPPOCIRE suppository base is a semi-synthetic glyceride. An example of a suitable biologically-compatible adhesive is hydroxypropyl methylcellulose (HPMC), available as METHOCEL* K15M from The Dow Chemical Company. An example of a suitable surfactant is polysorbate 80, available from Spectrum Chemical Manufacturing Corp. An example of a suitable penetration enhancer is LABRAFIL M 1944 C nonionic amphiphilic excipient, available from Gattefossé Corp.

For the purposes of this invention, any therapeutic agent that will treat the vaginal or other cavity, other mucosal tissue, or will be absorbed into a user's body through the vaginal or other epithelium for the purposes of treating diseases or conditions, promoting the growth of normal vaginal bacterial flora, or promoting vaginal or other health may be used. Examples of therapeutic agents include but are not limited to vitamins, minerals, hormones, moisturizers, antifungal agents, antibacterial agents, pro-biotics, botanicals, analgesics, prostaglandin inhibitors, prostaglandin synthetase inhibitors, leukotriene receptor antagonists, essential fatty acids, sterols, anti-inflammatory agents, vasodilators, chemotherapeutic agents, and agents to treat infertility.

Some therapeutic agents for use in this invention are absorbable through the vaginal epithelium and travel to the uterus by a unique portal of veins and arteries that are known to exist between the vagina, the cervix, and the uterus. This anastomosis eliminates first-pass metabolism by the liver, effectively delivering higher concentrations of the therapeutic agent to the uterus than would otherwise be available via oral dosing. Those of skill in the art know the efficacy of various therapeutic agents when introduced at a particular anatomical location. For example, when the therapeutic agent is selected to treat dysmenorrhea, it preferably is selected from the following group: nonsteroidal anti-inflammatory drugs (NSAIDs), prostaglandin inhibitors, COX-2 inhibitors, local anesthetics, calcium channel blockers, potassium channel blockers, β-adrenergic agonists, leukotriene blocking agents, smooth muscle inhibitors, and drugs capable of inhibiting dyskinetic muscle contraction.

Alternatively therapeutic agents modify the vaginal or other environment to enhance the wellness of this anatomical region. The benefits may be rather basic, for example increasing comfort by providing moisturization and/or lubricity. These benefits may also be more complex, for example modulating epithelial cell function to address vaginal atrophy. The beneficial therapeutic agents may reduce negative sensations such as stinging, burning, itching, etc, or introduce positive sensations to improve comfort.

Figure 4:
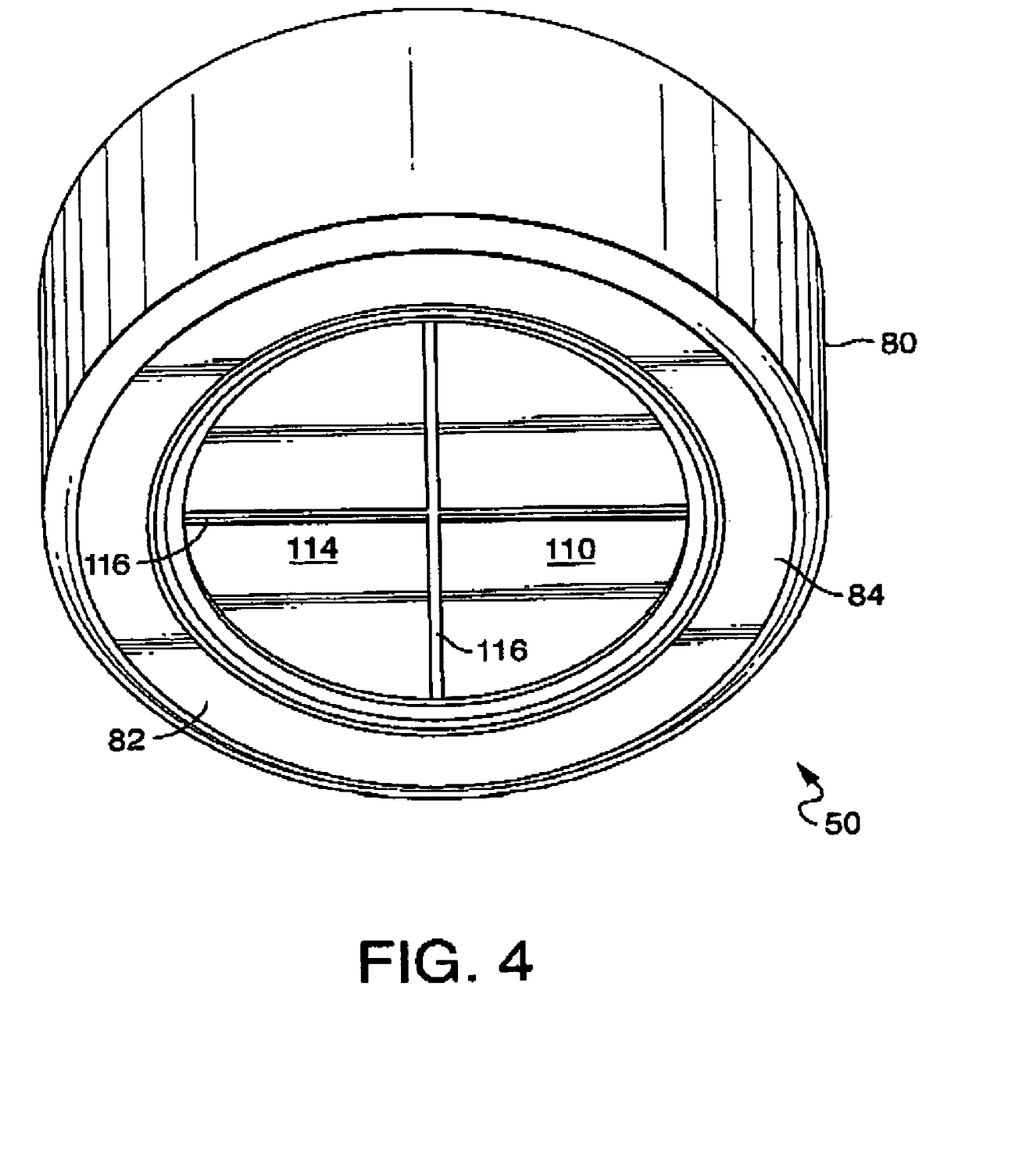
FIG. 4 is a perspective view of the dosage cap assembly of FIG. 3.

Referring to FIGS. 2-4, the dosage cap assembly 50 may also include a barrier seal 110 to seal the dosage form 45 within the tip cavity 74, or to seal the dosage form 45 and the tip 60 within the cap cavity 88. The barrier seal 110 may be a removable barrier seal 112, as shown in FIG. 2, or the barrier seal 110 may be affixed as a frangible barrier seal 114, as shown in FIGS. 3 and 4.

As shown in FIG. 2, the barrier seal 110 may be disposed at the open end 82 of the cap 80 such that the barrier seal 110 extends radially beyond the cap cavity 88 to contact the open end surface 84. The barrier seal 110 may project into the cap cavity 88 to improve the seal between the barrier seal 110 and the cap 80. The barrier seal 110 may also project a seal member 118 into the tip cavity 74, and in some embodiments the seal member 118 may engage the attachment end 62 of the tip 60. The barrier seal 110 may also include a circumferential groove 111 to assist the engagement with the attachment end 62 of the tip 60. The barrier seal 110 is affixed to the cap 80 at the open end surface 84 using any suitable adhesive or affixing means, including the use of hot-melt, water-based, solvent-based, or pressure-sensitive adhesives, mucilage, a thermal seal, ultrasonic bonding, pressure, friction, electrostatics, cling-like poly wraps, or surface energy effects The barrier seal 110 remains affixed during shipping and handling, but may be removed by a manufacturer or a consumer to reveal the contents of the cap 80. The barrier seal 110 may be formed from any suitable material, including foil, poly, film, film laminates, nonwovens, nonwoven laminates, protective materials such as TYVEK protective material, and any suitable elastomeric substance including rubber, or by a combination of these materials that will not adversely interact with the dosage form.

As shown in FIGS. 3 and 4, the frangible barrier seal 114 may also be disposed within the attachment end 62 of the tip 60. In this aspect, the barrier seal 114 remains in place when the tip 60 is attached to the first member 14 to create the medicated tampon assembly 10. The frangible barrier seal 114 includes a frangible or breakaway portion with break lines 116 allowing the barrier seal 110 to break into sections while each section remains attached to the tip 60. The frangible barrier seal 114 may be formed from any suitable material, including foil, poly, film, film laminates, nonwovens, nonwoven laminates, protective materials such as TYVEK protective material, and any suitable elastomeric substance including rubber, or by a combination of these materials that will not adversely interact with the dosage form.

Returning to FIG. 1, the dosage form 45, dosage cap assembly 50, and the tampon assembly 40 are combined to form the medicated tampon assembly 10. A dosage cap assembly 50 including a dosage form 45 is axially aligned with a tampon assembly 40. The dosage cap assembly 50 and the tampon assembly 40 are moved toward each other using minimal force to cause the engagement mechanism of the dosage cap assembly 50 and the first member 14 to engage, resulting in the tip 60 becoming permanently attached to the first member 14. The medicated tampon assembly 10 may then be packaged and shipped. Alternatively, the tampon assembly 40 and the dosage cap assembly 50 with dosage form 45 may be packaged separately and shipped together or separately. These may later be combined by an assembler or a consumer.

More specifically, the various components of the medicated tampon assembly 10 may be manufactured and assembled in a variety of ways, but generally focus on three subassemblies: the tampon assembly 40, the dosage cap assembly 50, and the dosage form 45.

The dosage form 45 may be produced by the same manufacturer as the manufacturer of the tampon assembly 40. The dosage form 45 may also be produced by a separate manufacturer and provided to the tampon manufacturer in any suitable manner. As an example, a dosage form manufacturer with a facility specifically designed for pharmaceutical manufacturing that meets current regulatory and quality requirements for drugs and/or devices, as appropriate, may produce the dosage forms 45 under conditions such that homogeneity, concentration, and purity of the dosage form 45 are closely controlled, and such that production is in accordance with applicable regulations. The dosage form 45 may then be sealed and shipped to the manufacturer of either the tampon assembly 40 or the dosage cap assembly 50. In this manner, the dosage form 45 is produced by a manufacturer with appropriate experience, and the tampon manufacturer may be relieved of establishing a pharmaceutical-production facility. This process is described in more detail in co-pending U.S. patent application Ser. No. 10/335,816 filed on Dec. 31, 2002 and titled "Medicated Tampon".

Likewise, the dosage cap assembly 50 including a dosage form 45 may be produced by the same manufacturer as the manufacturer of the tampon assembly 40. The dosage cap assembly 50 including a dosage form 45 may also be produced by a separate manufacturer and provided to the tampon manufacturer in any suitable manner. As an example, a pharmaceutical manufacturer with a facility specifically designed for pharmaceutical manufacturing that meets current regulatory and quality requirements for drugs and/or devices, as appropriate, may produce dosage cap assemblies 50 including dosage forms 45 under conditions such that homogeneity, concentration, and purity of the dosage form 45 are closely controlled, and such that production is in accordance with applicable regulations. The dosage cap assembly 50 including the dosage form 45 may then be sealed and shipped to the tampon manufacturer. The tampon manufacturer may then apply the dosage cap assembly 50 including a dosage form 45 to a tampon assembly 40 under appropriately-controlled conditions. In this manner, the dosage cap assembly 50 with a dosage form 45 is produced by a manufacturer with appropriate experience, and the tampon manufacturer is relieved of establishing a pharmaceutical-production facility.

In another aspect of the present invention, the tampon assembly 40 may be produced by a manufacturer different from the manufacturer of the dosage cap assembly 50 and both assemblies (40, 50) may be shipped to the manufacturer of the dosage form 45 for manufacture of the medicated tampon assembly 10. In another aspect of the present invention, the medicated tampon assembly 10 is produced by a manufacturer different from the manufacturer of the dosage form 45, the manufacturer of the tampon assembly 40, and the manufacturer of the dosage cap assembly 50.

In any case, the dosage form 45, the dosage cap assembly 50, and the tampon assembly 40 are each manufactured. The dosage form 45 and dosage cap assembly 50 are combined and sealed if appropriate, and then the dosage cap assembly 50 (with dosage form 45) is combined with a tampon assembly 40, by either a manufacturer or by a consumer.

In a different aspect of the present invention, the tampon assembly 40 and the dosage cap assembly 50 with dosage form 45 may be packaged separately. Both may then be provided to a consumer, either separately or in one package or kit. The consumer may also obtain the dosage cap assembly 50 and the tampon assembly 40 from separate manufacturers. In either case, either assembly may include instructions for use of a medicated tampon assembly 10. Such instructions may include information regarding when a medicated tampon assembly 10 is appropriate to use, standard pharmaceutical information regarding the dosage form 45 and therapeutic agent(s) contained therein, and directions regarding the method for properly combining the dosage cap assembly 50 and the tampon assembly 40. The consumer will be instructed to remove both a tampon assembly 40 and a dosage cap assembly 50 from their packaging. The consumer will then remove the barrier seal 110 from the dosage cap assembly 50 if a removable barrier seal 112 is present. The consumer will then be instructed to attach the dosage cap assembly 50 to the tampon assembly 40 by whatever method is appropriate for the type of engagement mechanism 76 is present such that the tip 60 becomes engaged with the tampon assembly 40. Finally, the consumer will be instructed to remove the cap 80 from the medicated tampon assembly 10 and use the medicated tampon assembly 10 as one would use a standard tampon.

In a different aspect of the present invention, a consumer may be provided with a dosage cap assembly 50 including a dosage form 45, along with a tampon assembly 40 that does not include a tampon 20. The assembly and use in this case will be similar to that of the complete medicated tampon assembly 10, but the consumer will be using the dosage form 45 alone without the tampon 20.

In use, and referring to FIG. 1, the medicated tampon assembly 10 functions because the second member 18 is telescopically movable relative to the first member 14. As the second member 18 is pushed into the first member 14, the tampon 20, if one is present, or the second member 18, if a tampon 20 is not present, is forced forward against the dosage form 45, which is thereby forced against the pleats or petals 66. The contact by the dosage form 45 causes the petals 66 to radially open to a diameter that is sufficient to allow the dosage form 45 and the tampon 20, if present, to be expelled from the first member 14. With the dosage form 45 and the tampon 20, if present, properly positioned in the vaginal or other cavity, the tampon applicator 12 with the attached tip 60 is withdrawn and properly discarded.

In the case where the dosage cap assembly 50 includes a frangible barrier seal 114, as the second member 18 is pushed into the first member 14, the tampon 20, if one is present, or the second member 18, if a tampon 20 is not present, is forced forward against the frangible barrier seal 114, causing the frangible barrier seal 114 to break along the break lines 116. The petal-like sections formed between the break lines 116 bend to allow the tampon 20, if one is present, or the second member 18, if a tampon 20 is not present, to pass through unimpeded. The tampon 20, if one is present, or the second member 18, if a tampon 20 is not present, is then forced forward against the dosage form 45, which is thereby forced against the pleats or petals 66. The contact by the dosage form 45 causes the petals 66 to radially open to a diameter that is sufficient to allow the dosage form 45 and the tampon 20, if present, to be expelled from the first member 14. Again, with the dosage form 45 and the tampon 20, if present, properly positioned in the vaginal or other cavity, the tampon applicator 12 with the attached tip 60 is withdrawn and properly discarded.

Once the tampon 20, if present, is properly positioned in the vaginal or other cavity, the tampon body 34 absorbs menses and other bodily fluids, and the dosage form 45 delivers the therapeutic agent to the vaginal or other epithelium for local or topical therapeutic action or from there, the therapeutic agent may be transferred to the uterus by normal bodily functions to relieve the condition to be treated.

The invention has been described with reference to various specific and illustrative aspects and techniques. However, it should be understood that many variations and modifications may be made while remaining within the spirit and scope of the invention.

Accordingly, this invention is intended to embrace all such alternatives, modifications and variations that fall within the spirit and scope of the appended claims.

We claim:

1. A dosage cap assembly for use with an applicator assembly, the dosage cap assembly comprising:
    a tip comprising
        an outer surface,
        an attachment end,
        an open tip second end opposite the attachment end, and
        an inner surface defining a tip cavity, wherein the attachment end of the tip includes an engagement mechanism selected from the group consisting of a snap ring, conventional screw threads, quarter-turn threads, a mechanical latch, and an escapement-type mechanism;
    a cap having an inner surface defining a cap cavity, the inner surface generally conforming to the outer surface of the tip, and wherein the cap has an open end surface;
    a dosage form disposed within the tip cavity; and
    a removable barrier seal affixed to the cap at the open end surface, wherein the removable barrier seal is completely removed from the cap prior to use.

2. The dosage cap assembly of claim 1, wherein the cap cavity is sized such that the tip may be disposed within the cap cavity.

3. The dosage cap assembly of claim 1, wherein the tip second end includes a plurality of flexible petals with gaps therebetween.

4. The dosage cap assembly of claim 3, wherein the cap includes projections projecting from the inner surface of the cap, wherein the projections are positioned to align with and generally block the gaps.

5. The dosage cap assembly of claim 1, wherein the tip second end includes a plurality of flexible petals having frangible portions therebetween.

6. A delivery device comprising:
    an applicator assembly having a first member with a receiving end and an insertion end and an inner tube slidably received in the receiving end;
    a dosage cap assembly comprising a tip and a cap; wherein the tip comprises an outer surface and an inner surface, the inner surface defining a tip cavity; and the cap comprises an inner surface defining a cap cavity;
    wherein a dosage form is disposed within the tip cavity, and the tip is disposed within the cap cavity; and wherein the cap has an open end surface having a removable barrier seal disposed thereon such that the removable barrier seal projects into the cap cavity;
    an engagement mechanism for attaching the tip to the applicator, the engagement mechanism having a first portion and a second portion, wherein one of the tip and the insertion end includes the first portion of the engagement mechanism, and the other of the tip and the insertion end includes the second portion of the engagement mechanism.

7. The device of claim 6, wherein the engagement mechanism is selected from a snap ring, conventional screw threads, quarter-turn threads, a mechanical latch, and an escapement-type mechanism.

8. The device of claim 6, wherein the applicator includes a tampon disposed therein.

\* \* \* \* \*